United States Patent [19]

Breuer et al.

[11] 3,996,219
[45] Dec. 7, 1976

[54] 3-HETEROTHIO DERIVATIVES OF (α-THIOCARBONYLAMINO) CEPHALOSPORINS

[75] Inventors: Hermann Breuer; Uwe D. Treuner, both of Regensburg, Germany

[73] Assignee: E. R. Squibb & Sons, Inc., Princeton, N.J.

[22] Filed: May 28, 1975

[21] Appl. No.: 581,446

[52] U.S. Cl. .................. 260/243 C; 260/332.2 A; 260/516; 260/534 S; 424/246
[51] Int. Cl.² ............. C07D 501/22; C07D 501/24; C07D 501/36
[58] Field of Search ................................ 260/243 C

[56] References Cited
UNITED STATES PATENTS

| 3,766,175 | 10/1973 | Lemieux et al. | 260/243 C |
| 3,769,281 | 10/1973 | Chauvette | 260/243 C |
| 3,819,621 | 6/1974 | Morimoto et al. | 260/243 C |
| 3,855,211 | 12/1974 | Bruer et al. | 260/243 C |

OTHER PUBLICATIONS

Takano et al., "Chemical Abstracts," vol. 71, (1969) abst. 124,914.

Primary Examiner—Nicholas S. Rizzo
Assistant Examiner—David E. Wheeler
Attorney, Agent, or Firm—Lawrence S. Levinson; Merle J. Smith

[57] ABSTRACT

3-Heterothio(α-thiocarbonylamino)cephalosporin derivatives of the general formula

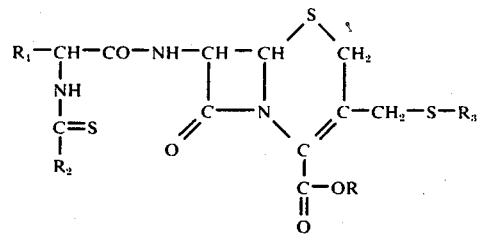

wherein R is hydrogen, lower alkyl, phenyl-lower alkyl, tri(lower alkyl)silyl, trihaloethyl, a salt forming ion or the group

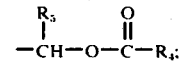

$R_1$ is hydrogen, lower alkyl, cyclo-lower alkyl, unsaturated cyclo-lower alkyl, phenyl, substituted phenyl or thienyl; $R_2$ and $R_5$ each is hydrogen or lower alkyl; $R_3$ is a five or six membered nitrogen, sulfur and/or oxygen containing ring system; and $R_4$ is lower alkyl, phenyl or phenyl-lower alkyl; are useful as antibacterial agents.

14 Claims, No Drawings

3-HETEROTHIO DERIVATIVES OF (α-THIOCARBONYLAMINO) CEPHALOSPORINS

SUMMARY OF THE INVENTION

This invention relates to new 3-heterothio-(α-thiocarbonylamino)cephalosporin derivatives of the formula

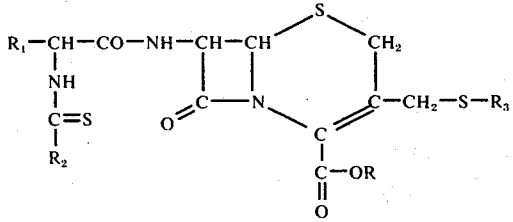

R represents hydrogen, lower alkyl, phenyl-lower alkyl, tri(lower alkyl)silyl, trihaloethyl, a salt forming ion or the group

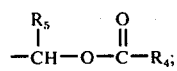

$R_1$ represents hydrogen, lower alkyl, cyclo-lower alkyl, unsaturated cyclo-lower alkyl, phenyl, substituted phenyl wherein the phenyl substituents are lower alkyl, lower alkoxy, hydroxy, halogen, amino, ureido or methylsulfonylamino, or thienyl; $R_2$ and $R_5$ each represents hydrogen or lower alkyl; $R_3$ represents a five or six-membered heterocycle including thiadiazole, oxadiazole, triazole, thiatriazole, tetrazole and their lower alkyl ($R_6$) substituted analogs; $R_4$ represents lower alkyl, phenyl or phenyl-lower alkyl.

The preferred members within each group are as follows: R is hydrogen, alkali metal, diphenylmethyl or

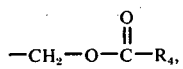

especially hydrogen, pivaloyloxymethyl, sodium or potassium; $R_1$ is hydrogen, phenyl or thienyl, especially phenyl or thienyl; $R_2$ is hydrogen or methyl; $R_3$ is preferably (lower alkyl)tetrazole or (lower alkyl)thiadiazole, especially wherein the lower alkyl group is methyl; $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, the $C_1$ to $C_4$ members and especially methyl and ethyl being preferred. The lower alkoxy groups are of the same kind.

The phenyl-lower alkyl radicals include a phenyl ring attached to a lower alkyl group of the kind described above as well as those containing two phenyl groups such as diphenylmethyl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine or a cyclo-lower alkylamine, like dicyclohexylamine, etc.

The halogens are the four common halogens, of which chlorine and bromine are preferred. In the case of trihaloethyl group represented by R, 2,2,2-trichloroethyl is preferred.

$R_3$ is thiadiazole, oxadiazole, triazole, thiatriazole, tetrazole and the lower alkyl substituted analogs of each of these except thiatriazole, especially 1,3,4-thiadiazole, 1,2,4-thiadiazole, tetrazole, 5-methyl-1,3,4-thiadiazol-2-yl, 3-methyl-1,2,4-thiadiazol-5-yl and 1-methyl-tetrazol-5-yl. The heterocyclics have, in particular, these structures:

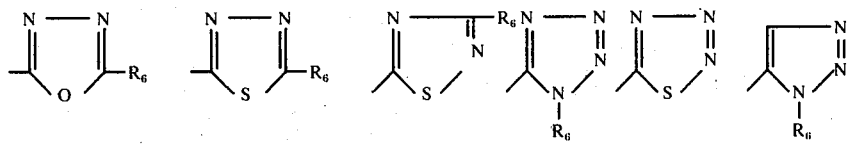

wherein $R_6$ is hydrogen or lower alkyl, especially methyl.

The new cephalosporin derivatives of this invention are produced by several methods. According to one method, a 7-aminocephalosporanic acid (7-ACA) derivative of the formula

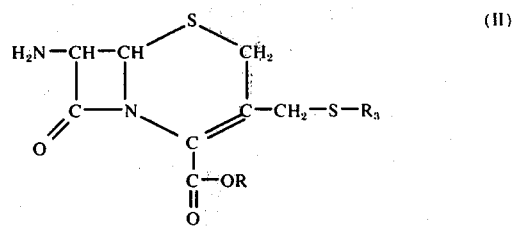

is reacted with an acid of the formula

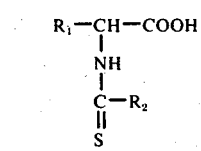

or an activated derivative like an activated ester or mixed anhydride, or in the presence of a coupling agent like dicyclohexylcarbodiimide.

One preferred synthesis comprises reacting the acid of formula III with the diphenylmethyl ester of the 7-ACA derivative of formula II and then hydrolyzing the ester with trifluoroacetic acid and anisole to obtain the free carboxyl group in the 4-position.

The reaction between the 7-aminocephalosporanic acid compound and the acid of formula III can be carried out, for example, by dissolving or suspending the acid in an inert organic solvent such as chloroform, tetrahydrofuran, methylene chloride, dioxane, benzene or the like, and adding, at a reduced temperature of about 0°–5° C, about an equimolar amount of the 7-ACA compound in the presence of an activating compound such as dicyclohexylcarbodiimide. The product of the reaction is then isolated by conventional procedures, e.g., by concentration or evaporation of the solvent. If a derivative of the 7-aminocephalosporanic acid compound, such as the diphenylmethyl ester is used, the free acid is obtained by hydrolysis, e.g., with trifluoroacetic acid or the like. Salts can then be derived from the free acid.

According to another embodiment, an acid of formula III is reacted with a compound of the formula

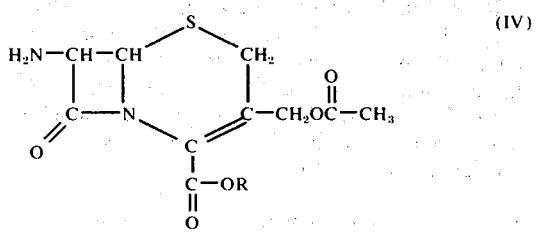

preferably wherein R is diphenylmethyl. When R is the preferred diphenylmethyl group, it is converted to the free acid with trifluoroacetic acid and anisole. The product of the formula

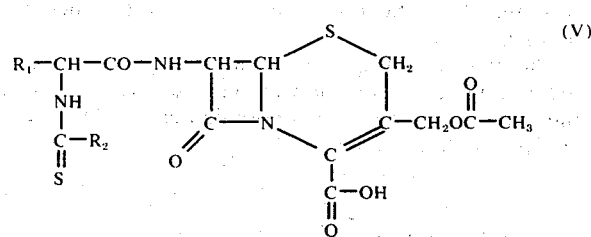

is then reacted with a thiol of the formula

in basic solution, e.g., at a pH of about 7.8, to obtain the product of formula I.

According to still another embodiment, a compound of the formula

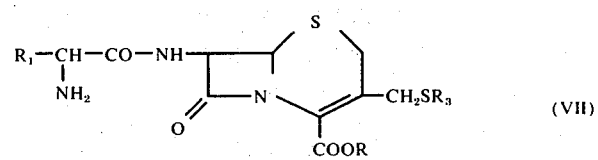

is made to react with a compound of the formula

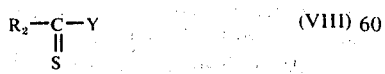

wherein Y is an activating group like-O-lower alkyl, halogen or —S—CH$_2$—COOH, in a solvent like methylene chloride in the presence of triethylamine, then adding a source of hydrogen ion like hydrogen sulfide.

When R is the acyloxymethyl group

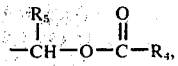

this group can be introduced into the 7-aminocephalosporanic acid moiety prior to the reaction with the acid of formula III or the activated derivative by treatment with one to two moles of a halomethyl ester of the formula

wherein hal is halogen, preferably chlorine or bromine, in an inert organic solvent such as dimethylformamide, acetone, dioxane, benzene or the like, at about ambient temperature or below.

The acid of formula III is produced by reacting an ester, preferably the diphenylmethyl ester of an α-amino acid of the formula

with a thioformate

(wherein Y is lower alkyl) in an inert solvent like tetrahydrofuran at about ambient temperature and adding a source of hydrogen ion, e.g., hydrogen sulfide and finally treating with trifluoroacetic acid and anisole.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus*, *Salmonella schottmuelleri*, *Pseudomonas aeruginosa*, *Proteus vulgaris*, *Escherichia coli* and *Streptococcus pyogenes*. They are useful as antibacterial agents, e.g., to combat infections due to organisms such as those named above, and in general they can be utilized in a manner similar to cephradine and other cephalosporins. For example, a compound of formula I or a physiologically acceptable salt thereof can be used in various animal species affected by infections of such bacterial origin in an amount of about 1 to 75 mg/kg daily, orally or parenterally, in single or two to four divided doses.

Up to about 500 mg. of a compound of formula I or a physiologically acceptable salt thereof is administered by incorporating in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

3-[[(5-methyl-1,3,4-thiadiazol-2-yl)thio]methyl]-7-amino-8-oxo-5-thia-1-azabicyclo[4.2.0]oct-2-ene-2-carboxylic acid A mixture of 13.6 g. (0.05 M) of 7-aminocephalosporanic acid (7-ACA) in 100 ml. of water and 50 ml. of acetone are brought to pH 8 with sodium hydroxide while stirring. 7.5 g. (0.057 M) of 2-methyl-1,3,4-thiadiazole-5-thiol are added and the mixture is heated at 80° for four hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 2

3-[[(3-Methyl-1,2,4-thiadiazol-5-yl)thio]methyl]-7-amino-8-oxo-5-thia-1-azabicyclo[4.2.0]oct-2-ene-2-carboxylic acid By substituting 3-methyl-1,2,4-thiadiazole-5-thiol for the 2-methyl-1,3,4-thiadiazole-5-thiol in the procedure of Example 1, 11.6 g. of 3-[[(3-methyl-1,2,4-thiadiazol-5-yl)thio]methyl]-7-amino-8-oxo-5-thia-1-azabicyclo[4.2.0]oct-2-ene-2-carboxylic acid, m.p. 186° (dec.) are obtained.

EXAMPLE 3

3-[[(1-Methyl-1H-tetrazol-5-yl)thio]methyl]-7-amino-8-oxo-5-thia-1-azabicyclo[4.2.0]oct-2-ene-2-carboxylic acid By substituting 0.057 M of 1-methyl-1H-tetrazole-5-thiol for the 2-methyl-1,3,4-thiadiazole-5-thiol in the procedure of Example 1, 3-[[(1-methyl-1H-tetrazol-5-yl)thio]methyl]-7-amino-8-oxo-5-thia-1-azabicyclo[4.2.0]oct-2-ene-2-carboxylic acid is obtained.

EXAMPLE 4

7-Amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester 18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain the 10 g. of the product, 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester, as a light brown powder, m.p. 157°–159°. The product is recrystallized from tetrahydrofuran/petroleum ether.

7-Amino-3-[[(3-methyl-1,2,4-thiadiazol-5-yl)thio]methyl]-7-amino-8-oxo-5-thia-1-azabicyclo[4.2.0]oct-2-ene-2-carboxylic acid, diphenylmethyl ester is similarly obtained by substituting the product of Example 2.

EXAMPLE 5

7-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester The product, 7-amino-3-[[(1-methyl-1H-tetrazol-5-yl)thio]methyl]-8-oxo-5-thia-1-azabicyclo[4.2.0]oct-2-enecarboxylic acid, diphenylmethyl ester, m.p. 168°–169° (dec.), is obtained by the procedure of Example 4 utilizing as starting material 7-amino-3-[[(1-methyl-1H-tetrazol-5-yl)-thio]methyl]-8-oxo-5-thia-1-azabicyclo[4.2.0]oct-2-ene-2-carboxylic acid.

EXAMPLE 6

3-[[(1-methyl-1H-tetrazol-5-yl)thio]methyl]-8-oxo-7β-[[phenyl[(thioxomethyl)amino]acetyl]amino]-5-thia-1-azabicyclo-[4.2.0]oct-2-ene-2-carboxylic acid and sodium salt a. 7β-[[[[(4-methoxyphenyl)methoxy]carbonyl]amino]phenyl-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 3.78 g. (0.012 mol.) of [[[(4-methoxyphenyl)methoxy]-carbonyl]amino]benzeneacetic acid (prepared as described in U.S. Pat. No. 3,560,489, Feb. 2, 1971) are dissolved in 100 ml. of tetrahydrofuran and added to a solution of 4.95 g. (0.01 mol.) of 7-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 50 ml. of methylene chloride. The mixture is cooled to 0°–5° and at this temperature a solution of 2.27 g. (0.011 mol.) of dicyclohexylcarbodiimide is added dropwise. The mixture is stirred for 90 minutes at 0°–5° and 90 minutes at room temperature. The precipitated dicyclohexylurea (2.4 g.) if filtered off. The filtrate is concentrated and the residue is taken up in a mixture of ethyl acetate and tetrahydrofuran (3:1). The organic phase is washed once with sodium bicarbonate solution and twice with water, then decolorized with activated carbon, dried with magnesium sulfate, filtered and concentrated to a small volume. The precipitated product is filtered under suction. 5.5 g. of 7β-[[[[(4-methoxyphenyl)methoxy]carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, are obtained, m.p. 145°–150° (dec.). By concentrating the mother liquor and adding ether, an additional 0.7 g. of product is obtained.

b. 7β-[(aminophenylacetyl)amino]-3-[[(1-methyl-1H-tetrazol-5-yl)thio]methyl]-8-oxo-5-thia-1-azabicyclo-[4.2.0]oct-2-ene-2-carboxylic acid, trifluoroacetate salt 3.7 g. of the product of part a are added at 0°–5°to a mixture of 74 ml. trifluoroacetic acid and 22 ml. of anisole. After 10 minutes. the trifluoroacetic acid is evaporated under vacuum and ether is added to the residue. 2.6 g. of 7β-[(aminophenylacetyl)amino]-3-[[1-methyl-1H-tetrazol-5-yl)thio]]methyl-8-oxo-5- thia-azabicyclo[4.2.0]-oct-2-ene-2-carboxylic acid, trifluoroacetate salt is obtained.

c. 3-[[(1-methyl-1H-tetrazol-5-yl)thio]methyl]-8-oxo-7β-[[phenyl[(thioxomethyl)amino]acetyl]amino]-5-thia-1-azabicyclo[4.2.0]oct-2-ene-2-carboxylic acid 1.8 g. of the product of part b are suspended in 31 ml. of ethylthioformate, cooled to 0°–5°and 6.8 ml. of a solution of triethylamine in methylene chloride (2.5 ml. of triethylamine and sufficient methylene chloride to make 25 ml.) are added. After 15 minutes, a stream of hydrogen sulfide is passed in for 15 minutes with stirring. After three hours, petroleum ether is added until precipitation is complete, and then the mixture is filtered under suction. The triethylamine salt of 3-[[(1-methyl-1H-tetrazol-5-yl)thio]methyl]-8-oxo-7β-[[phenyl[(thioxomethyl)-amino]acetyl]amino]-5-thia-1-azabicyclo[4.2.0]oct-2-ene-2-carboxylic acid thus obtained is dissolved in 30 ml. of water, the solution is adjusted to pH 6.5 with sodium bicarbonate, filtered and the filtrate is acidified to pH 1.5 with 2N hydrochloric acid. 0.9 g. of product is obtained, m.p. 158°–160° (dec.).

d. 3-[[(1-methyl-1H-tetrazol-5-yl)thio]methyl]-8-oxo-7-β-[[phenyl[(thioxomethyl) amino]acetyl]amino]-5-thia-1-azabicyclo[4.2.0]oct-2-ene-2-carboxylic acid, sodium salt 0.51 g. of 3-[[(1-methyl-1H-tetrazol-5-yl)thio]methyl]-8-oxo-7β-[[phenyl[(thioxomethyl)amino]acetyl]amino]-5-thia-1-azabicyclo[4.2.0]oct-2-ene-2-carboxylic acid from part c are brought into solution with 10 ml. of a 0.1 N sodium bicarbonate solution and the clear solution is freeze dried. A quantitative yield of the sodium salt is obtained, m.p. 180°–190° (dec.).

EXAMPLE 7

7-[D-2-[[(2-thienyl)-2-(thioxomethyl)amino]acetyl]amino]-3-[[(1-methyl-1H-tetrazol-5-yl)thio]methyl]-8-oxo-5-thia-1-azabicyclo[4.2.0]oct-2-ene-2-carboxylic acid a. 8.0 g. of magnesium oxide are suspended in 200 ml. of water. 15.7 g. of D-2-(2-thienyl)glycine are added to the suspension followed by a solution of 22.8 g. of p-methoxybenzyloxycarbonylazide in 200 ml. dioxane. The mixture is stirred for 3 days at room temperature. The reaction mixture is then filtered and the filtrate is extracted once with 125 ml. of diethyl ether. The ether layer is then discarded. The aqueous phase is cooled to 5°–10°, layered with about 150 ml. of ethyl acetate and acidifed with 2N hydrochloric acid to pH 2.5. After separating the layers, the aqueous phase is extracted again with 100 ml. of ethyl acetate. The combined ethyl acetate solutions are washed once with water, dried over magnesium sulfate and evaporated. The oily residue crystallizes on treatment with petroleum ether. The yield amounts to 30.8 gms. of crude material. After recrystallization from ethyl acetate/petroleum ether, 25.2 gms. of D-α-[[[(4-methoxyphenyl)methoxy]carbonyl]amino]-2-thiopheneacetic acid are obtained, m.p. 66°–69°. The material is usually contaminated with a small amount of ethyl acetate which cannot be removed at 35° in vacuum. The material obtained free from ethyl acetate has a melting point 89°–92°, $[\alpha]_D^{25} = -62.2°$ ($c = 1$, tetrahydrofuran)

b. 7β-[[[[(4-methoxyphenyl)methoxy]carbonyl]amino]-(2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester The product of part a and 7-amino-3-[[(1-methyl-1H-tetrazol-5-yl)thio]methyl]-8-oxo-5-thia-1-azabicyclo[4.2.0]-oct-2-ene-2-carboxylic acid diphenylmethyl ester are dissolved in 650 ml. of absolute tetrahydrofuran and the solution is cooled to 0°. At this temperature, a solution of 7.3 gms. of dicyclohexylcarbodiimide in 60 ml. of absolute tetrahydrofuran is added dropwise over a period of about 20 minutes. The mixture is stirred at 0° for two hours and an additional two hours at room temperature. The dicyclohexylurea which precipitates is removed by filtration. The filtrate is concentrated in vacuum. The residue is dissolved in ethyl acetate, washed with saturated sodium bicarbonate solution, then with water and dried with magnesium sulfate. After filtration, the filtrate is left overnight in the refrigerator. The reaction product crysallizes. On filtration 12.2 gms. of 7β-[[[[(4-methoxyphenyl)methoxy]carbonyl]amino]-2-thienyl)acetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester are obtained, m.p. 126° (dec.). The filtrate is evaporated to dryness. Treatment with ethyl acetate yields a second crop of 2.6 gms. A third crop of 2.6 gms. is obtained when the filtrate is evaporated, dissolved in a small amount of ethyl acetate, precipitated with petroleum ether and again treated with ethyl acetate.

c. 7-[D-2-amino-2-(2-thienyl)acetamido]-3-[[(1-methyl-1-H-tetrazol-5-yl)thio]methyl]-8-oxo-5-thia-1-azabicyclo-[4.2.0]oct-2-ene-2-carboxylic acid, trifluoroacetate salt 11.5 gms. of the product of part b are mixed with 30 ml. of anisole, cooled to 0°–5° and 150 ml. of trifluoroacetic acid are added. The solution is stirred for 10 minutes at this temperature. Then the solvent is stripped off in vacuum and the residue is treated with diethyl ether. 8.6 gms. of 7-[D-2-amino-2-(2-thienyl)acetamido]-3-[[(1-methyl-1-H-tetrazol-5-yl)thio]methyl]-8-oxo-5-thia-1-azabicyclo[4.2.0]oct-2-ene-2-carboxylic acid, trifluoroacetate salt are obtained.

d. 7-[D-2-[(2-thienyl)-2-(thioxomethyl)amino]acetyl]amino-3-[[(1-methyl-1H-tetrazol-5-yl)thio]methyl]-8-oxo-5-thia-1-azabicyclo[4.2.0]oct-2-ene-2-carboxylic acid The product of part c is reacted with ethylthioformate in the presence of triethylamine according to the procedure of Example 6 c to obtain 7-[D-2-[[(2-thienyl)-2-(thioxomethyl)amino]acetyl]amino]-3-[[(1-methyl-1H-tetrazol-5-yl)thio]methyl]-8-oxo-5-thia-1-azabicyclo[4.2.0]oct-2-ene-2-carboxylic acid, m.p. 130° (dec.).

EXAMPLE 8

7-[DL-2-[[(3-thienyl)-2-(thioxomethyl)amino]acetyl]amino]methyl-[[(1H-tetrazol-5-yl)thio]methyl]-8-oxo-5-thia-1-azabycyclo-[4.2.0]oct-2-ene-2-carboxylic acid 7-[DL-2-Amino-2-(3-thienyl)acetamido]-3-[[(1-methyl-1H-tetrazol-5-yl)thio]methyl]-8-oxo-5-thia-1-azabicyclo[4.2.0]-oct-2-ene-2-carboxylic acid, trifluoroacetate salt (prepared by the procedure of Example 7 but substituting DL-2-(3-thienyl)glycine for the D-2-(2-thienyl)glycine) is reacted with ethylthioformate according to the procedure of Example 6c to obtain 7-[DL-2-[(3-thienyl)-2-(thioxomethyl)amino]acetyl]amino-3-[[(1-methyl-1H-tetrazol-5-yl)thio]methyl]-8-oxo-5-thia-1-azabicyclo[4.2.0]oct-2-ene-2-carboxylic acid.

EXAMPLE 9

α-[(Thioxomethyl)amino]benzene acetic acid, diphenylmethyl ester

A solution of 15.9 g. (0.05 mol.) of α-phenylglycine, diphenylmethyl ester, and 9 g. (0.01 mol.) of ethylthioformate in 50 ml. of tetrahydrofuran is stirred overnight at room temperature. Then a stream of hydrogen sulfide is passed into the solution for ten minutes, the reaction mixture is permitted to stand overnight, the concentrated and petroleum ether is added to the residue. 16.9 g. of α-[(thioxomethyl)-amino]benzeneacetic acid, diphenylmethyl ester, crystallizes. The crude product is recrystalized from methanol, m.p. 129°–130°.

EXAMPLE 10

α-[(Thioxomethyl)amino]benzeneacetic acid 3.61 g. (0.01 mol.) of α-[(thioxomethyl)amino]-benzeneacetic acid, diphenylmethyl ester are added to a mixture of 30 ml. of trifluoroacetic acid and 5 ml. of anisole at 0°–5° and the mixture is stirred for ten minutes. The mixture is concentrated, sodium bicarbonate solution is added to the residue and the aqueous phase is extracted with ether. This is then layered over with fresh ether, acidified and the aqueous phase is extracted twice with ether. Concentration of the ether solution yields α-[(thioxomethyl)amino]benzeneacetic acid as an oily residue.

EXAMPLE 11

7-[D-2-phenyl-2-[(thioxomethyl)amino]acetyl]amino-3-[(5-methyl-1,3,4-thiadiazol-2-yl)thio]methyl-8-oxo-5-thia-1-azabicyclo[4.2.0]oct-2-ene-2-carboxylic acid, diphenyl-methyl ester To a solution of 0.01 mol. of 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester and 0.012 mol. of α-[(thioxomethyl)amino]benzeneacetic acid in 100 ml. of tetrahydrofuran is added at 0°–5° a solution of 0.011 mol. of dicyclohexylcarbodiimide in 20 ml. of tetrahydrofuran. The mixture is stirred for 90 minutes at 0°–5° and 90 minutes at room temperature, then filtered and concentrated. The residue is taken up in ethyl acetate, shaken with sodium bicarbonate solution and with water, dried with magnesium sulfate and again concentrated. Petroleum ether is added to the residue and 7-[D-2-phenyl-2-[[(thioxomethyl)amino]acetyl]amino]-3-[(5-methyl-1,3,4-thiadiazol-2-yl)thio]methyl-8-oxo-5-thia-1-azabicyclo[4.2.0]oct-2-ene-2-carboxylic acid, diphenylmethyl ester is obtained as a beige-brown amorphous powder.

EXAMPLE 12

7-[D-2-phenyl-2[(thioxomethyl)amino]acetyl]amino-[3-(5-methyl-1,3,4-thiadiazol-2-yl)thio]methyl-8-oxo-5-thia-1-azabicyclo-[4.2.0]oct-2-ene-2-carboxylic acid 2 g. of the product of Example 11 are added to a mixture of 20 ml. of trifluoroacetic acid and 1 ml. of anisole at 0°–5°, stirred for 10 minutes, concentrated and ether is added to the residue. 7-[D-2-phenyl-2-[[thioxo-methyl]amino]acetyl]amino-3-[[(5-methyl-1,3,4-thiadiazol-2-yl)thio]methyl]-8-oxo-5-thia-1-azabicyclo[4.2.0]oct-2-ene-2-carboxylic acid is obtained as an amorphous powder.

EXAMPLE 13

7-[D-2-[(2-thienyl)-2-[(1-thioxoethyl)amino]acetyl]amino]-[(3-methyl-1,2,4-thiadiazol-5-yl)thio]methyl-8-oxo-5-thia-1-azabicyclo[4.2.0]oct-2-ene-2-carboxylic acid 0.01 mol. of 7-[D-2-amino-2-(2-thienyl)acetamido]-3-[[(3-methyl-1,2,4-thiadiazol-5-yl)thio]methyl]-8-oxo-5-thia-1-azabicyclo[4.2.0]oct-2-ene-2-carboxylic acid, trifluoroacetate salt (prepared by the procedure of Example 7, but substituting 3-[[(3-methyl-1,2,4-thiadiazol-5-yl)thio]methyl]-7-amino- 8-oxo-5-thia-1-azabicyclo[4.2.0]oct-2-ene-2-carboxylic acid, diphenylmethyl ester in part b) is brought into solution with triethylamine in methylene chloride and 0.015 mol. of [(1-thioxoethyl)thio]acetic acid (prepared as described in U.S. Pat. No. 3,341,518) is added. The reaction mixture is permitted to stand for three hours and worked up according to the procedure of Example 7 to obtain 7-[D-2-[(2-thienyl)-2-[(1-thioxoethyl)amino]acetyl]amino]-3-[[3-methyl-1,2,4-thiadiazol-5-yl)thio]methyl]-8-oxo-5-thia-1-azabicyclo[4.2.0]-oct-2-ene-2-carboxylic acid.

EXAMPLES 14 – 38

The products below are obtained by the procedure of Example 7 (Example 6 d to obtain the salt) from the α-amino acid

and the diphenylmethyl ester of one of the following [produced by the procedure of Examples 1 and 4 (Example 6d to obtain a salt)]:

a. 3-[[(5-methyl-1,3,4-thiadiazolyl-2-yl)thio]methyl]-7-amino-8-oxo-5-thia-1-azabicyclo[4.2.0]oct-2-ene-2-carboxylic acid
b. 3-[[(1-methyl-1H-tetrazol-5-yl)thio]methyl]-7-ACA
c. 3-[[(1,3,4-oxadiazol-2-yl)thio]methyl]-7-ACA
d. 3-[[(5-ethyl-1,3,4-oxadiazol-2-yl)thio]methyl]-7-ACA
e. 3-[[(1,2,3,4-tetrazol-5-yl)thio]methyl]-7-ACA
f. 3-[[(1-ethyl-1H-tetrazol-5-yl)thio]methyl]-7-ACA
g. 3-[[(1,2,4-thiadiazol-3-yl)thio]methyl]-7-ACA
h. 3-[[(5-butyl-1,2,4-thiadiazol-3-yl)thio]methyl]-7-ACA
i. 3-[[(3-methyl-1,2,4-oxadiazol-5-yl)thio]methyl]-7-ACA
j. 3-[[(2-methyl-1,3,4-thiadiazol-5-yl)thio]methyl]-7-ACA
k. 3-[[(1,2,4,-thiadiazol-5-yl)thio]methyl]-7-ACA
l. 3-[[(5-methyl-1,2,4-thiadiazol-2-yl)thio]methyl]-7-ACA
m. 3-[[(2-methyl-1H-tetrazol-5-yl)thio]methyl]-7-ACA
n. 3-[[(1,3,4-thiadiazol-2-yl)thio]methyl]-7-ACA
o. 3-[[(1,2,3,4-thiatriazol-5-yl)thio]methyl]-7-ACA
p. 3-[[(1,2,3-triazol-5-yl)thio]methyl]-7-ACA
q. 3-[[(1-methyl-1,2,3-triazol-5-yl)thio]methyl]-7-ACA

| Example | |
|---|---|
| 14 | 7-[D-2-phenyl-2-[[(1-thioxoethyl)amino]acetyl]amino]-3-[[(1,3,4-thiadiazol-2-yl)thio]methyl]-8-oxo-5-thia-1-azabicyclo[4.2.0]oct-2-ene-2-carboxylic acid. |
| 15 | 7-[D-2-phenyl-2-[[(1-thioxobutyl)amino]acetyl]amino]-3-[[(1,3,4-oxadiazol-2-yl)thio]methyl]-8-oxo-5-thia-1-azabicyclo[4.2.0]oct-2-ene-2-carboxylic acid. |
| 16 | 7-[D-2-[[(1-thioxoethyl)amino]propionyl]amino]-3-[[(5-ethyl-1,3,4-oxadiazol-2-yl)thio]methyl]-8-oxo-5-thia-1-azabicyclo[4.2.0]oct-2-ene-2-carboxylic acid |
| 17 | 7-[D-2-phenyl-2-[[(thioxomethyl)amino]acetyl]amino]-3-[[(1,2,4-thiadiazol-5-yl)thio]methyl]-8-oxo-5-thia-1-azabicyclo[4.2.0]oct-2-ene-2-carboxylic acid |
| 18 | 7-[D-2-[(1-thioxopropyl)amino]butyramido]-3-[[(1,2,4-thiadiazol-3-yl)thio]methyl]-8-oxo-5-thia-1-azabicyclo-[4.2.0]oct-2-ene-2-carboxylic acid |
| 19 | 7-[D-2-phenyl-2-[[(thioxomethyl)amino]acetyl]amino]-3-[[(5-butyl-1,2,4-thiadiazol-3-yl)thio]methyl]-8-oxo-5-thia-1-azabicyclo[4.2.0]oct-2-ene-2-carboxylic acid |
| 20 | 7-[D-2-[[(thioxomethyl)amino]acetyl]amino]-3-[[(1,2,3,4-tetrazol-5-yl)thio]methyl]-8-oxo-5-thia-1-azabicyclo-[4.2.0]oct-2-ene-2-carboxylic acid |
| 21 | 7-[D-2-cyclohexyl-2-[[(thioxomethyl)amino]acetyl]amino]-3-[[(3-methyl-1,2,4-oxadiazol-5-yl)thio]methyl]-8-oxo-5-thia-1-azabicyclo[4.2.0]oct-2-ene-2-carboxylic acid |
| 22 | 7-[D-2-(1-cyclohexenyl)-2-[[(thioxomethyl)amino]acetyl]-amino]-3-[[(1-ethyl-1H-tetrazol-5-yl)thio]methyl]-1-azabicyclo[4.2.0]oct-2-ene-2-carboxylic acid |
| 23 | 7-[D-2-cyclopentyl-2-[[(1-thioxoethyl)amino]acetyl]-amino]-3-[[(1-ethyl-1H-tetrazol-5-yl)thio]methyl]-8-oxo-5-thia-1-azabicyclo[4.2.0]oct-2-ene-2-carboxylic acid |
| 24 | 7-[D-2-[(1-thioxopropyl)amino]-2-(2-thienyl)acetyl]-amino]-3-[[2-(2-methyl-1,3,4-thiadiazol-5-yl]thio]-methyl]-8-oxo-5-thia-1-azabicyclo[4.2.0]oct-2-ene-2-carboxylic acid |
| 25 | 7-[D-2-[[[(1-thioxoethyl)amino]-2-(1,4-cyclo-hexadien-1-yl)acetyl]amino]-3-[[(5-methyl-1,3,4-thiadiazol-2-yl)thio]methyl]-8-oxo-5-thia-1-azabicyclo-[4.2.0]oct-2-ene-2-carboxylic acid and potassium salt |
| 26 | 7-[D-2-[(p-tolyl)-2-[[(thioxomethyl)amino]acetyl]-amino]-3-[[(1,3,4-oxadiazol-2-yl)thio]methyl]-8-oxo-5-thia-1-azabicyclo[4.2.0]oct-2-ene-2-carboxylic acid and sodium salt |
| 27 | 7-[D-2-[(2-hydroxyphenyl)-2-(thioxomethyl)amino]acetyl]-amino]-3-[[(5-ethyl-1,3,4-oxadiazol-2-yl)thio]methyl]--8-oxo-5-thia-1-azabicyclo[4.2.0]oct-2-ene-2-carboxylic acid |
| 28 | 7-[D-2-[[(4-aminophenyl)-2-(1-thioxoethyl)amino]acetyl]-amino]-3-[[(1,2,3,4-tetrazol-5-yl)thio]methyl]-8-oxo-5-thia-1-azabicyclo[4.2.0]oct-2-ene-2-carboxylic acid, phenyl ester |
| 29 | 7-[D-2-(4-ureidophenyl)-2-[[(thioxomethyl)amino]acetyl]-amino]-3-[[(1,2,4-thiadiazol-5-yl)thio]methyl]-8-oxo-5-thia-1-azabicyclo[4.2.0]oct-2-ene-2-carboxylic acid, triethylamine salt |
| 30 | 7-[D-2-[4-(methylsulfonylamino)phenyl]-2-[[(thioxo-methyl)amino]acetyl]amino]-3-[[(1,2,4-thiadiazol-3-yl)thio]methyl]-8-oxo-5-thia-1-azabicyclo[4.2.0]oct-2-ene-2-carboxylic acid pivaloyloxymethyl ester |
| 31 | 7-[D-[[2-(2-chlorophenyl)-2-(thioxoethyl)amino]acetyl]-amino]-3-[[2-methyl-1,3,4-thiadiazol-5-yl)thio]methyl]-8-oxo-5-thia-1-azabicyclo[4.2.0]oct-2-ene-2-carboxylic acid trimethylsilyl ester |
| 32 | 7-[D-2-[[(2-thienyl)-2-(1-thioxoethyl)amino]acetyl]-amino]-3-[[(5-methyl-1,2,4-thiadiazol-2-yl)thio]methyl]-8-oxo-5-thia-1-azabicyclo[4.2.0]oct-2-ene-2-carboxylic acid, (1-acetyloxy)ethyl ester |
| 33 | 7-[DL-2-(3-thienyl)-2-[[(thioxomethyl)amino]acetyl]-amino]-3-[[(1-methyl-1H-tetrazol-5-yl)thio]methyl]-8-oxo-5-thia-1-azabicyclo[4.2.0]oct-2-ene-2-carboxylic acid diphenylmethyl ester |
| 34 | 7-[DL-2-phenyl-2-[[(thioxomethyl)amino]acetyl]amino]-3-[[1,2,3,4-thiatriazol-5-yl)thio]methyl]-8-oxo-5-thia-1-azabicyclo[4.2.0]oct-2-ene-2-carboxylic acid, 2,2,2-trichloroethyl ester |
| 35 | 7-[DL-2-[[(thioxomethyl)amino]acetyl]amino]-3-[[(1,2,3-triazol-5-yl)thio]methyl]-8-oxo-5-thia-1-azabicyclo[4.2.0]oct-2-ene-2-carboxylic acid |
| 36 | 7-[D-2-(1,4-cyclohexadien-1-yl)-2-[[(thioxomethyl)-amino]acetyl]amino]-3-[[(1-methyl-1H-tetrazol-5-yl)-thio]methyl-8-oxo-5-thia-1-azabicyclo[4.2.0]oct-2-ene-2-carboxylic acid, methyl ester |
| 37 | 7-[DL-2-[[(1-thioxoethyl)amino]-2-(2-thienyl]-acetyl]amino]-3-[[(1-methyl-1H-tetrazol-5-yl)thio]-methyl]-8-oxo-5-thia-1-azabicyclo[4.2.0]oct-2-ene-2-carboxylic acid, benzyl ester |
| 38 | 7-[D-2-phenyl-2-[[(1-thioxoethyl)amino]acetyl]amino]-3-[[(1-methyl-1,2,3-triazol-5-yl)thio]methyl]-8-oxo-5-thia-1-azabicyclo[4.2.0]oct-2-ene-2-carboxylic acid and potassium salt |

What is claimed is:
1. A compound of the formula

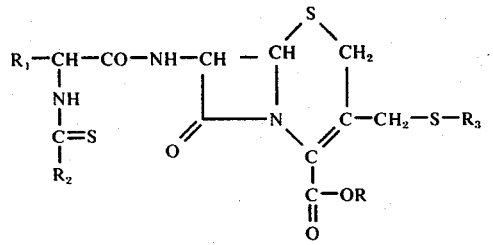

wherein R is hydrogen, lower alkyl, phenyl-lower alkyl, tri(lower alkyl)silyl, trihaloethyl,

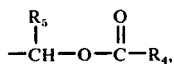

alkali metal, alkaline earth metal or (lower alkyl)amine; $R_1$ is thienyl or phenyl; $R_2$ and $R_5$ each is hydrogen or lower alkyl; $R_3$ is $R_6$-thiadiazole, $R_6$-oxadiazole, $R_6$-triazole, thiatriazole or $R_6$-tetrazole; $R_4$ is lower alkyl, phenyl or phenyl-lower alkyl; and $R_6$ is hydrogen or lower alkyl.

2. A compound as in claim 1 wherein $R_1$ is phenyl.
3. A compound as in claim 1 wherein $R_1$ is thienyl.
4. A compound as in claim 1 wherein $R_2$ is lower alkyl.
5. A compound as in claim 1 wherein $R_2$ is hydrogen.
6. A compound as in claim 1 wherein $R_3$ is 1-methyl-tetrazole.
7. A compound as in claim 1 wherein $R_3$ is methyl-thiadiazole.
8. A compound of the formula

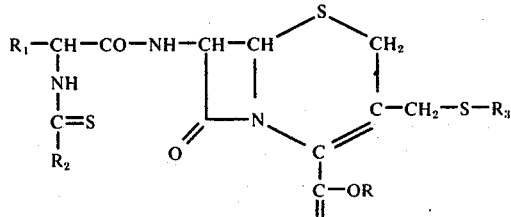

wherein R is hydrogen, alkali metal, diphenylmethyl or

$R_1$ is phenyl or thienyl; $R_2$ is hydrogen or methyl; $R_3$ is (lower alkyl) tetrazole or (lower alkyl)thiadiazole; $R_4$ is methyl or t-butyl.

9. A compound as in claim 1 wherein R and $R_2$ each is hydrogen, $R_1$ is phenyl and $R_3$ is (1-methyl-1H-tetrazol-5-yl).

10. A compound as in claim 1 wherein R and $R_2$ each is hydrogen; $R_1$ is 2-thienyl; and $R_3$ is 1-methyl-1H-tetrazol-5-yl.

11. A compound as in claim 1 wherein R and $R_2$ each is hydrogen, $R_1$ is 3-thienyl and $R_3$ is 1-methyl-1H-tetrazol-5-yl.

12. A compound as in claim 1 wherein R and $R_2$ each is hydrogen, $R_1$ is phenyl and $R_3$ is 5-methyl-1,3,4-thiadiazol-2-yl.

13. A compound as in claim 1 wherein R is hydrogen, $R_1$ is 2-thienyl, $R_2$ is methyl and $R_3$ is 3-methyl-1,2,4-thiadiazol-5-yl.

14. A compound as in claim 1 wherein R is alkali metal; $R_1$ is phenyl, $R_2$ is hydrogen and $R_3$ is 1-methyl-1H-tetrazol-5-yl.

* * * * *